US005792888A

United States Patent [19]

Subramanian

[11] Patent Number: 5,792,888
[45] Date of Patent: Aug. 11, 1998

[54] PROCESS FOR PHOSGENATION IN THE PRESENCE OF ACETONITRILE

[75] Inventor: N. Subramanian, Hercules, Calif.

[73] Assignee: Zeneca Limited, London, England

[21] Appl. No.: 577,958

[22] Filed: Dec. 22, 1995

Related U.S. Application Data

[63] Continuation of Ser. No. 397,444, May 1, 1995, abandoned.
[51] Int. Cl.[6] .................................................. C07C 51/58
[52] U.S. Cl. ............................................................ 562/857
[58] Field of Search .............................................. 562/857

[56] References Cited

U.S. PATENT DOCUMENTS 3,857,841 12/1974 Keil ......................................... 562/857

FOREIGN PATENT DOCUMENTS 0 220 516  5/1987  European Pat. Off. .
27 50 169  5/1978  Germany .

Primary Examiner—Paul J. Killos
Attorney, Agent, or Firm—Joel G. Ackerman; Joseph R. Snyder

[57] ABSTRACT

Phosgenation of carboxylic acids to the corresponding carboxylic acid chlorides in conducted in the presence of a solvent comprising acetonitrile.

13 Claims, No Drawings

PROCESS FOR PHOSGENATION IN THE PRESENCE OF ACETONITRILE

This application is a continuation of application Ser. No. 08/397,444, filed Mar. 1, 1995 abandoned.

FIELD OF THE INVENTION

This invention relates to the conduct of a process for phosgenation of a carboxylic acid to produce a carboxylic acid chloride by reacting the carboxylic acid with phosgene and particularly by conducting the reaction in the presence of acetonitrile as a solvent or co-solvent.

Usually such phosgenation is carried out in the presence of an organic solvent such as toluene or xylene, or mixtures thereof, with catalysts such as triethylamine or dimethylformamide (DMF). According to the present invention it has been determined that production of carboxylic acid chlorides by phosgenation of carboxylic acids can be conducted in the presence of acetonitrile as a solvent or co-solvent.

While acetonitrile is a common solvent for a number of reactions and procedures, those skilled in the art had considered it unsuitable for use in a phosgenation process as they believed that it would become chlorinated and/or that hydrogen cyanide would be generated during the reaction. However, surprisingly, these undesirable instances did not occur when acetonitrile was used in this process.

SUMMARY OF THE INVENTION

In one aspect, this invention comprises a process for the production of a carboxylic acid chloride by reaction of the corresponding carboxylic acid with phosgene in the presence of acetonitrile.

In a second aspect, this invention comprises a process for the production of N-substituted-5-(substituted phenoxy)-2-substituted benzoic acid sulphonamides by reaction of the corresponding benzoic acid with phosgene in the presence of acetonitrile to produce the corresponding benzoyl chloride, followed by the reaction of the benzoyl chloride with a substituted sulphonylamide in the presence of acetonitrile.

DESCRIPTION OF THE INVENTION

In a general aspect, this invention relates to the production of carboxylic acid chlorides by phosgenation of the corresponding carboxylic acid in the presence of acetonitrile as a solvent or co-solvent. The reaction may generally be expressed as

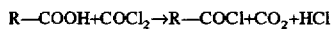

R—COOH+COCl$_2$→R—COCl+CO$_2$+HCl in which R is an organic group.

More particularly, this invention pertains to the production of acid chlorides of optionally substituted phenoxybenzoic and pyridyloxybenzoic acids, and even more particularly to the production of carboxylic acid chlorides of such acids having the formula

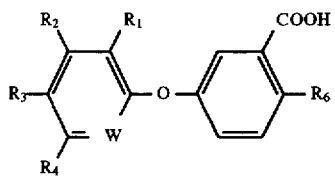

in which W is —C—R$_7$ or nitrogen; R$_1$, R$_2$, R$_3$, R$_4$, R$_5$ and R$_7$ are hydrogen, halogen or halomethyl, and R$_6$ is usually hydrogen or nitro. Most preferably R$_2$ and R$_4$ are hydrogen and W is —CH. One such acid is 5-(2-chloro-4-trifluoromethylphenoxy)-2-nitrobenzoic acid, also known as the herbicide acifluorfen.

In general, a phosgenation process is normally only carried out using aromatic solvents. This is primarily because to be useful as the solvent in phosgenation a material must possess three properties: a) the carboxylic acid must be soluble in it, b) the solvent must be non-reactive to the phosgene, and c) it must have a boiling point of over about 60° C. to function. Acetonitrile meets these requirements, as mentioned above. It had been considered unsuitable for use in phosgenation because it was believed that it would become chlorinated and/or release HCN.

However, in conducting experiments using acetonitrile as a solvent or co-solvent in the phosgenation of acifluorfen, I did not observe either the chlorination of the acetonitrile or generation of HCN.

The acetonitrile may be used as the sole solvent in the phosgenation process or as a co-solvent. As will be discussed below, depending on the utilization to be made of the carboxylic acid chloride, it may be advantageous to use acetonitrile as a co-solvent with, for instance, an aromatic solvent such as benzene, xylene or toluene.

For example, acifluorfen may be utilized as a starting material for production of another herbicide, 5-(2-chloro-4-trifluoromethylphenoxy)-N-methanesulphonyl-benzamide, also known as fomesafen. Alternatively, acifluorfen may be utilized for production of analogs of fomesafen, and other phenoxybenzoic, pyridyloxybenzoic and guinolineoxybenzoic acids may be used for production of their corresponding sulphonamides or other carboxylic acid derivatives.

In producing alkyl sulphonamide derivatives of such carboxylic acids, the carboxylic acid chloride is typically reacted with an alkyl sulphonylamide, for instance, methane-sulphonylamide, ethanesulphonylamide and the like. Aromatic solvents such as toluene may not be satisfactory for this step because, for instance, methanesulphonylamide is not soluble in toluene.

On the other hand, acetonitrile alone has not been found suitable for conducting this downstream reaction. The sulphonation step is carried out in the absence of water and requires a mixed two-solvent system containing, for example, acetonitrile and toluene or xylene. Without such a two-phase system it has been found that the reaction mixture becomes an unstirrable thick mass.

Thus, if the carboxylic acid chloride is to be used for subsequent production of a sulphonamide, it is advantageous to conduct the phosgenation in the presence of the same solvent to be used in the subsequent reaction, i.e., a mixture of acetonitrile and a hydrocarbon solvent, particularly an aromatic hydrocarbon solvent such as toluene or xylene (either a single isomer, or more commonly, a mixture of isomers). In such cases, the acetonitrile and aromatic solvent are used in a volume ratio respectively of from about 1:1 to about 2:1. The desired objective in this phosgenation step is a 15–30%, preferably 20%, solution of the acid in the mixed solvent. A particularly suitable solvent combination for the production of fomesafen from acifluorfen via its carboxylic acid chloride is a 1:1 weight ratio mixture of acetonitrile and aromatic solvent used in an amount in which the total weight ratio of solvents with respect to the acid chloride, is approximately 2:1. For convenience this mixture is referred to as a "2:2" mixture of acetonitrile and aromatic solvent. The invention is more particularly illustrated by the following examples.

EXAMPLE 1

This example illustrates the phosgenation of acifluorfen using acetonitrile as the sole solvent.

In a reactor there was placed a mixture of acifluorfen (|2-nitro-5-(2-chloro,4-trifluoromethylphenoxy)benzoic acid| (36.1 g, 0.10 mol), acetonitrile (108 ml) and dimethylformamide (DMF) (0.5 ml, 6 mmol). The mixture was heated to approximately 70° C. Then a total of 34 g (0.34 mol) phosgene was added in portions over a period of approximately two hours. At the end of this period, phosgene addition was stopped, the lines were vented with nitrogen and the mixture was maintained at the same temperature for an additional one hour, by which time the mixture had become almost amber in color.

There was obtained 138 ml of product, identified by gas chromatography as the acid chloride corresponding to acifluorfen (yield: 100% of theoretical).

EXAMPLE 2

This example demonstrates the phosgenation of acifluorfen using a solvent comprising a 1:1 ratio of acetonitrile and xylene (mixed isomers).

Similarly to Example 1, a reactor was loaded with 36.1 g (0.10 mol) acifluorfen, 55 ml (mixed isomers) xylene, 55 ml acetonitrile and 0.5 ml DMF. Then a total of 33 g (0.3 mol) phosgene was added over slightly less than four hours, the lines were vented and heating was continued for approximately ½ hour more. There was obtained 128 ml (100% of theoretical yield) of product, identified by gas chromatography as the carboxylic acid chloride of acifluorfen.

EXAMPLE 3

This example illustrates the process according to the invention using a solvent containing a volume ratio of acetonitrile: toluene of 1.8:1.

Similarly to Example 1, a reactor was charged with 72.2 g (0.2 mol) acifluorfen, 138 ml acetonitrile, 78 ml toluene and 1.0 ml DMF. Subsequently, 55 g (0.55 mol) phosgene was added over a period of approximately 2¼ hours. At the end of this period, the lines were vented and the mixture heated for a further 1¼ hour approximately. There was obtained 268 ml of solution which was identified by gas chromatography as containing the carboxylic acid chloride of acifluorfen.

EXAMPLE 4

This example illustrates the conduct of the process using a solvent comprising a 2:1 volume ratio of acetonitrile/toluene.

Similarly to Example 1, a reactor was charged with 72.2 g (0.2 mol) acifluorfen, 144 ml acetonitrile, 72 ml toluene and 1.0 ml DMF. Then, 55 g (0.55 mole) phosgene was added over a period of approximately 4¼ hours, the lines were vented and the reactor heated for another hour. There was obtained 270 ml of solution, identified by gas chromatography as containing the carboxylic acid chloride of acifluorfen.

EXAMPLE 5

This example illustrates the conduct of the process of this invention using acetonitrile and xylene in a 1:1 weight ratio, and a 2:1 overall volume ratio of solvents to acid chloride ("2:2" mixture).

Similarly to Example 1, a reactor was charged with 72.2 g (0.2 mol) acifluorfen, 192 ml acetonitrile, 172 ml xylenes (mixed isomers) and 0.31 ml (2 mol percent) DMF. Then, 58 g (0.57 mol) phosgene was added over a period of approximately 3½ hours, the lines were vented and heating continued for about one hour additional. There was a obtained 422 ml of solution containing the desired product, whose identity was confirmed by gas chromatography.

EXAMPLE 6

This example illustrates the conversion of the acid chloride to fomesafen.

A reactor was charged with methanesulphonamide (12.7 g, 0.13 mole), anhydrous potassium bicarbonate (34.1 g, 0.25 mole) and acetonitrile (200 ml), and was heated to 80° C. with stirring. To the mixture was slowly added 177 g (195 ml) of a solution of acifluorfen carboxylic acid chloride (0.1 mole) in a 2:2 acetonitrile-xylenes mixture, prepared as in Example 5. Addition was done over a period of 4 hours. After the addition was complete, the mixture was maintained at 80° for 1 hour. Then 150 ml water and 34 ml conc. HCl were added to adjust the pH to 1, and this mixture was phase separated. The organic phase was treated with 4% caustic to adjust the pH to 9.5, then heated to boil off the organic solvents. The aqueous solution was determined by analysis to contain fomesafen, in 90% yield.

What is claimed:

1. A process for the production of a carboxylic acid chloride by phosgenation of the corresponding carboxylic acid wherein said phosgenation is conducted in the presence of a solvent comprising acetonitrile.

2. A process according to claim 1 wherein the solvent comprises a mixture of acetonitrile and an aromatic hydrocarbon.

3. A process according to claim 2 wherein the solvent comprises a mixture of acetonitrile and toluene or one or more xylenes.

4. A process according to claim 2 in which the molar ratio of acetonitrile to aromatic hydrocarbon is from about 1:1 to about 1:2 by volume.

5. A process according to claim 4 wherein the ratio of acetonitrile to aromatic hydrocarbon is about 1:1 by volume.

6. A process according to claim 4 wherein the ratio of acetonitrile to aromatic hydrocarbon is about 1:1 by weight and the total weight ratio of solvents to carboxylic acid chloride is about 2:1.

7. A process according to claim 1 in which the carboxylic acid has the formula.

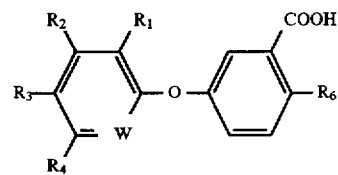

in which W is —CR$_7$ or N; R$_1$, R$_2$, R$_3$, R$_4$ and R$_5$ and R7 are hydrogen, halogen, or halomethyl and R$_6$ is hydrogen or nitro.

8. A process according to claim 7 in which W is C—R$_7$.

9. A process according to claim 7 in which R$_2$ and R$_4$ are hydrogen.

10. A process according to claim 9 in which R$_1$ is chloro, R$_3$ is trifluoromethyl, W is C—R$_7$, R$_2$, R$_4$ and R$_5$ are each hydrogen and R$_6$ is nitro.

11. A process according to claim 2 further comprising reacting the carboxylic acid chloride with an alkylsulphonylamide to produce the corresponding alkanesulphonamide.

12. A process according to claim 11 in which the carboxylic acid chloride has the formula

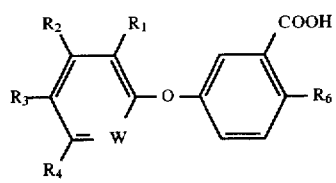

in which $R_1$ is chloro, $R_3$ is trifluoromethyl, W is —C—$R_7$, $R_2$, $R_4$ and $R_5$ are each hydrogen and $R_6$ is nitro, and the alkylsulphonylamide is methylsulphonylamide or ethylsulphonylamide.

13. A process according to claim 12 in which the solvent comprises acetonitrile and an aromatic hydrocarbon in a 1:1 weight ratio, and the total solvent to carboxylic acid weight ratio is 2:1.

* * * * *